United States Patent
Lin et al.

(10) Patent No.: US 9,861,776 B2
(45) Date of Patent: *Jan. 9, 2018

(54) ULTRASOUND-BASED TRACHEAL TUBE PLACEMENT DEVICE AND METHOD

(71) Applicant: Covidien LP, Boulder, CO (US)

(72) Inventors: Andy S. Lin, Boulder, CO (US); Youzhi Li, Longmont, CO (US)

(73) Assignee: Covidien LP, Mansfield, MA (US)

( * ) Notice: Subject to any disclaimer, the term of this patent is extended or adjusted under 35 U.S.C. 154(b) by 878 days.

This patent is subject to a terminal disclaimer.

(21) Appl. No.: 13/907,199

(22) Filed: May 31, 2013

(65) Prior Publication Data
US 2013/0267839 A1    Oct. 10, 2013

Related U.S. Application Data

(63) Continuation of application No. 12/511,504, filed on Jul. 29, 2009, now Pat. No. 8,522,787.

(51) Int. Cl.
*A61M 16/04* (2006.01)
*A61B 8/08* (2006.01)
(Continued)

(52) U.S. Cl.
CPC ........ *A61M 16/0434* (2013.01); *A61B 8/0833* (2013.01); *A61B 8/0841* (2013.01);
(Continued)

(58) Field of Classification Search
CPC .......... A61M 16/0057; A61M 16/0434; A61M 25/1011; A61M 16/04; A61M 16/0443; A61M 16/0459; A61M 16/0483; A61M 16/0488; A61M 2205/3375; A61M 2205/502; A61B 8/0841; A61B 8/4483; A61B 8/461; A61B 8/0833; A61B 8/4472
USPC ............ 128/200.24, 200.26, 207.14–207.18; 604/93.01, 97.01, 102.01, 102.03, 103, 604/103.05–103.1; 600/424, 431–435, 600/458
See application file for complete search history.

(56) References Cited

U.S. PATENT DOCUMENTS 4,083,369 A * 4/1978 Sinnreich ................. 604/103.06
4,263,921 A   4/1981 Trugillo
(Continued)

FOREIGN PATENT DOCUMENTS

WO   2009099766   8/2009

OTHER PUBLICATIONS

Roberts, James R. et al., Proper Depth of Placement of Oral Endotracheal Tubes in Adults Prior to Radiographic Confirmation, Academic Emergency Medicine, Jan. 1995, pp. 20-24, vol. 2, No. 1.
(Continued)

*Primary Examiner* — (Jackie) Tan-Uyen T Ho
*Assistant Examiner* — Joseph D Boecker

(57) ABSTRACT

An inflatable balloon cuff may be adapted to seal a patient's trachea when associated with an endotracheal tube. These cuffs may include features that facilitate detection or visualization of the cuff, for example with ultrasound devices, to ensure proper placement of the cuff and the tube. Such surface features may include particular types of materials or shaped or protruding features that may be detected in the environment of the trachea.

9 Claims, 5 Drawing Sheets

(51) Int. Cl.
*A61M 16/00* (2006.01)
*A61B 8/00* (2006.01)

(52) U.S. Cl.
CPC ............ *A61B 8/4483* (2013.01); *A61B 8/461* (2013.01); *A61M 16/0057* (2013.01); *A61M 16/04* (2013.01); *A61M 16/0443* (2014.02); *A61M 16/0459* (2014.02); *A61B 8/4472* (2013.01); *A61M 16/0488* (2013.01); *A61M 2205/502* (2013.01)

(56) References Cited

U.S. PATENT DOCUMENTS

| | | | |
|---|---|---|---|
| 4,344,436 A | 8/1982 | Kubota | |
| 4,383,534 A | 5/1983 | Peters | |
| 4,401,124 A * | 8/1983 | Guess | A61B 8/0833 600/458 |
| 4,416,289 A | 11/1983 | Bresler | |
| 4,431,005 A | 2/1984 | McCormick | |
| 4,445,501 A | 5/1984 | Bresler | |
| 4,567,882 A | 2/1986 | Heller | |
| 4,582,061 A * | 4/1986 | Fry | A61B 8/0833 600/431 |
| 4,943,770 A | 7/1990 | Ashley-Rollman et al. | |
| 4,989,611 A | 2/1991 | Zanetti et al. | |
| 5,033,466 A * | 7/1991 | Weymuller, Jr. | 128/207.15 |
| 5,081,997 A * | 1/1992 | Bosley et al. | 600/458 |
| 5,099,845 A | 3/1992 | Besz et al. | |
| 5,193,544 A | 3/1993 | Jaffe | |
| 5,201,314 A * | 4/1993 | Bosley, Jr. | A01K 85/00 600/431 |
| 5,383,466 A * | 1/1995 | Partika | A61B 8/0833 600/459 |
| 5,400,771 A | 3/1995 | Pirak et al. | |
| 5,423,745 A * | 6/1995 | Todd | A61M 25/1002 604/103.08 |
| 5,425,370 A | 6/1995 | Vilkomerson | |
| 5,425,382 A | 6/1995 | Golden et al. | |
| 5,445,144 A | 8/1995 | Wodicka et al. | |
| 5,560,351 A | 10/1996 | Gravenstein et al. | |
| 5,622,169 A | 4/1997 | Golden et al. | |
| 5,645,065 A | 7/1997 | Shapiro et al. | |
| 5,785,051 A * | 7/1998 | Lipscher | A61B 5/06 128/200.26 |
| 5,879,297 A | 3/1999 | Haynor et al. | |
| 5,902,238 A | 5/1999 | Golden et al. | |
| 6,053,870 A * | 4/2000 | Fulton, III | A61B 17/3421 600/458 |
| 6,120,442 A | 9/2000 | Hickey | |
| 6,129,668 A | 10/2000 | Haynor et al. | |
| 6,132,379 A | 10/2000 | Patacsil et al. | |
| 6,161,537 A | 12/2000 | Gravenstein et al. | |
| 6,164,277 A | 12/2000 | Merideth | |
| 6,216,028 B1 | 4/2001 | Haynor et al. | |
| 6,253,770 B1 | 7/2001 | Acker et al. | |
| 6,263,230 B1 | 7/2001 | Haynor et al. | |
| 6,332,089 B1 | 12/2001 | Acker et al. | |
| 6,349,720 B1 | 2/2002 | Clark | |
| 6,453,190 B1 | 9/2002 | Acker et al. | |
| 6,517,492 B2 | 2/2003 | Koblanski | |
| 6,672,308 B1 | 1/2004 | Gaspari | |
| 6,705,319 B1 | 3/2004 | Wodicka et al. | |
| 6,860,264 B2 | 3/2005 | Christopher | |
| 6,964,660 B2 * | 11/2005 | Maguire | A61B 18/00 606/41 |
| 7,803,150 B2 * | 9/2010 | Chang | A61B 17/24 604/514 |
| 7,867,169 B2 * | 1/2011 | Webler | A61M 25/0009 600/459 |
| 8,116,858 B2 | 2/2012 | Koblanski | |
| 8,196,584 B2 * | 6/2012 | Maguire et al. | 128/207.15 |
| 8,245,708 B2 | 8/2012 | Smaldone et al. | |
| 8,522,787 B2 * | 9/2013 | Lin et al. | 128/207.15 |
| 8,540,666 B2 * | 9/2013 | Rioux | A61M 37/00 604/93.01 |
| 8,617,079 B2 * | 12/2013 | Mitchell | A61B 8/0833 600/437 |
| 2002/0074002 A1 | 6/2002 | Tung et al. | |
| 2003/0125726 A1 * | 7/2003 | Maguire | A61B 18/00 606/41 |
| 2004/0078215 A1 * | 4/2004 | Dahlin | G06F 19/322 705/2 |
| 2004/0221853 A1 | 11/2004 | Miller | |
| 2006/0036164 A1 | 2/2006 | Wilson et al. | |
| 2006/0081255 A1 * | 4/2006 | Miller | A61B 8/0833 128/207.14 |
| 2006/0210605 A1 * | 9/2006 | Chang | A61B 17/24 424/434 |
| 2007/0137652 A1 | 6/2007 | Qureshi et al. | |
| 2007/0142770 A1 * | 6/2007 | Rioux | A61M 37/00 604/93.01 |
| 2008/0000482 A1 * | 1/2008 | Maguire et al. | 128/207.15 |
| 2008/0039715 A1 | 2/2008 | Wilson et al. | |
| 2008/0051758 A1 * | 2/2008 | Rioux | A61B 17/12022 604/509 |
| 2010/0160731 A1 * | 6/2010 | Giovannini | A61B 17/3478 600/117 |
| 2010/0168684 A1 * | 7/2010 | Ryan | A61B 10/0233 604/272 |
| 2011/0030694 A1 * | 2/2011 | Schaner | A61M 16/04 128/207.15 |
| 2012/0215074 A1 * | 8/2012 | Krimsky | A61B 1/012 600/301 |
| 2014/0058253 A1 * | 2/2014 | Prough | A61B 5/0095 600/424 |

OTHER PUBLICATIONS

Pollard, Richard J. MD et al., Endotracheal Tube Location Verified Reliably by Cuff Palpation, Anesthesia and Analgesia, 1995, pp. 135-138.
Cardoso, Monica M. S. C. MD et al., Portable Devices Used to Detect Endotracheal Intubation During Emergency Situations: A Review, Critical Care Medicine, May 1998, pp. 957-964, vol. 26, Issue 5.
Locker, Gottfried J. MD et al., Assessment of the Proper Depth of Endotracheal Tube Placement with the Trachlight, Journal of Clinical Anesthesia, Aug. 1998, pp. 389-393, vol. 10.
Gaspari, Romolo J. MD et al., Magnetically Guided Orotracheal Intubation, Academic Emergency Medicine, Mar. 2001, pp. 285-287, vol. 8, No. 3.
Salem, M. Ramez MD, Verification of Endotracheal Tube Position, Anesthesiology Clinics of North America, Dec. 2001, pp. 1-18, vol. 19, Issue 4.
Juan, Eduardo J. et al., Miniature Acoustic Guidance System for Endotracheal Tubes, IEEE Transactions on Biomedical Engineering, Jun. 2002, pp. 584-596, vol. 49, No. 6.
Kristensen, Michael S. MD, The Parker Flex-Tip Tube Versus a Standard Tube for Fiberoptic Orotracheal Intubation, Anesthesiology, Feb. 2003, pp. 354-358, vol. 98, No. 2.
Kohase, Hikaru DDS, PhD et al., Endotracheal Intubation Device with a Charge Couple Device Camera, Anesthesiology, Dec. 2003, pp. 432-434, Issue 96.
Makino, Hiroshi MD et al., The Effects of Tracheal Tube Tip Design and Tube Thickness on Laryngeal Pass Ability During Oral Tube Exchanger with an Introducer, Anesthesia and Analgesia, Dec. 2003, pp. 285-288, Issue 97.
Chun, Rosaleen, MDm FRCPC et al., Where's the Tube? Evaluation of Hand-held Ultrasound in Confirming Endotracheal Tube Placement, Prehospital and Disaster Medicine, Nov. 2004, pp. 366-369, vol. 19, No. 4.
Monitoring of Intubation and Ventilation During Resuscitation, http://clinicaltrials.gov/ct2/show/NCT00204217,ClinicalTrials.gov, Aug. 2010, pp. 1-3.
O'Connor, Christopher J. MD et al., Identification of Endotracheal Tube Malpositions Using Computerized Analysis of Breath Sounds via Electronic Stethoscopes, Anesthesia and Analgesia, Dec. 2005, pp. 735-739, Issue 101.

(56) References Cited

OTHER PUBLICATIONS

Sehata, H et al., Tracheal Intubation using a new CCD Camera-Equipped Device: A Report of Two Cases with a Difficult Intubation, Acta Anaesthesiologica Scandinavica, Dec. 2005, pp. 1218-1220, Issue 49.
Weaver, Blake et al., Confirmation of Endotracheal Tube Placement after Intubation Using the Ultrasound Sliding Lung Sign, Academic Emergency Medicine, Mar. 2006, pp. 239-244, Issue 13.
Kaplan, M. B. et al., Seeing is Believing: the Importance of Video Laryngoscopy in Teaching and in Managing the Difficult Airway, Surgical Endoscopy and Other Interventional Techniques, Mar. 2006, pp. S479-S483, Issue 20.
Fridman, Ofer, Visual Sensor Provides a Breath of Fresh Air for Medical Ventilation, Medical Design Technology, Jul. 2006, pp. 11-13.
Schwarz, Uwe MD, Validation of Supra-Sternal Tube-Tip Palpatation (SSTTP), http://clinicaltrials.gov/ct2/show/NCT00690508, ClinicalTrials.gov, Aug. 2010, pp. 1-4.
Karsli, Cengiz, Head Movement Effect on Different Tracheal Tubes, http://clinicaltrials.gov/ct2/show/NCT00687583, ClinicalTrials.gov, Aug. 2010, pp. 1-3.
Wichakook, Warit et al., Magnetic Endotracheal Tube Imaging Device, 30th Annual International IEEE EMBS Conference, Vancouver, Canada, Aug. 20-24, 2008, pp. 985-988.
Gravenstein, D. et al., Breakthroughs in Endotracheal Tube Design and Verification of Tracheal Placement, University of Florida, Office of Technology Licensing, pp. 1-2.
Juan, Eduardo J, Minature Acoustic Guidance System for Endotracheal Tubes, Dissertation from University of Purdue, p. 1.
Raphael, David T. MD et al., Ultrasound Confirmation of Endotracheal Tube Placement, Journal of Clinical Ultrasound, Sep. 1987, pp. 459-462, Issue 15.

\* cited by examiner

ULTRASOUND-BASED TRACHEAL TUBE PLACEMENT DEVICE AND METHOD

CROSS-REFERENCE TO RELATED APPLICATIONS

This application is a continuation of U.S. Pat. No. 8,522,787 filed Jul. 29, 2009, the contents of which are hereby incorporated by reference in their entirety.

BACKGROUND

The present disclosure relates to medical devices, and more particularly, to airway products, such as tracheal tubes and cuffs.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, tracheal tubes may be used to control the flow of air or other gases through a patient's trachea. Such tracheal tubes may include endotracheal (ET) tubes, tracheotomy tubes, or transtracheal tubes. In many instances, it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

For example, a patient may be intubated by insertion of an endotracheal tube through the patient's mouth and into the trachea. Often, such intubation procedures may be performed during medical emergencies or during critical care situations. As such, healthcare providers may balance a desire for speed of intubation with a desire for accurate placement of the tube within the trachea. However, proper placement of a tracheal tube may be complex. In certain situations, placement may be aided with visualization of the trachea performed during laryngoscopy. During an intubation procedure, a practitioner may employ a lighted laryngoscope during introduction of the endotracheal tube. However, often the visualization of the trachea is poor because of patient secretions that may obscure the laryngoscope. In addition, such visualization during introduction of the tube may not account for ongoing changes in the tube's position within the trachea that may occur when a patient coughs, which may dislodge a tube from its desired location, or when a patient moves or is jostled within a care setting, which may change the position or angle of the tube within the trachea.

BRIEF DESCRIPTION OF THE DRAWINGS

Advantages of the disclosure may become apparent upon reading the following detailed description and upon reference to the drawings in which.

DETAILED DESCRIPTION

Figure 1:
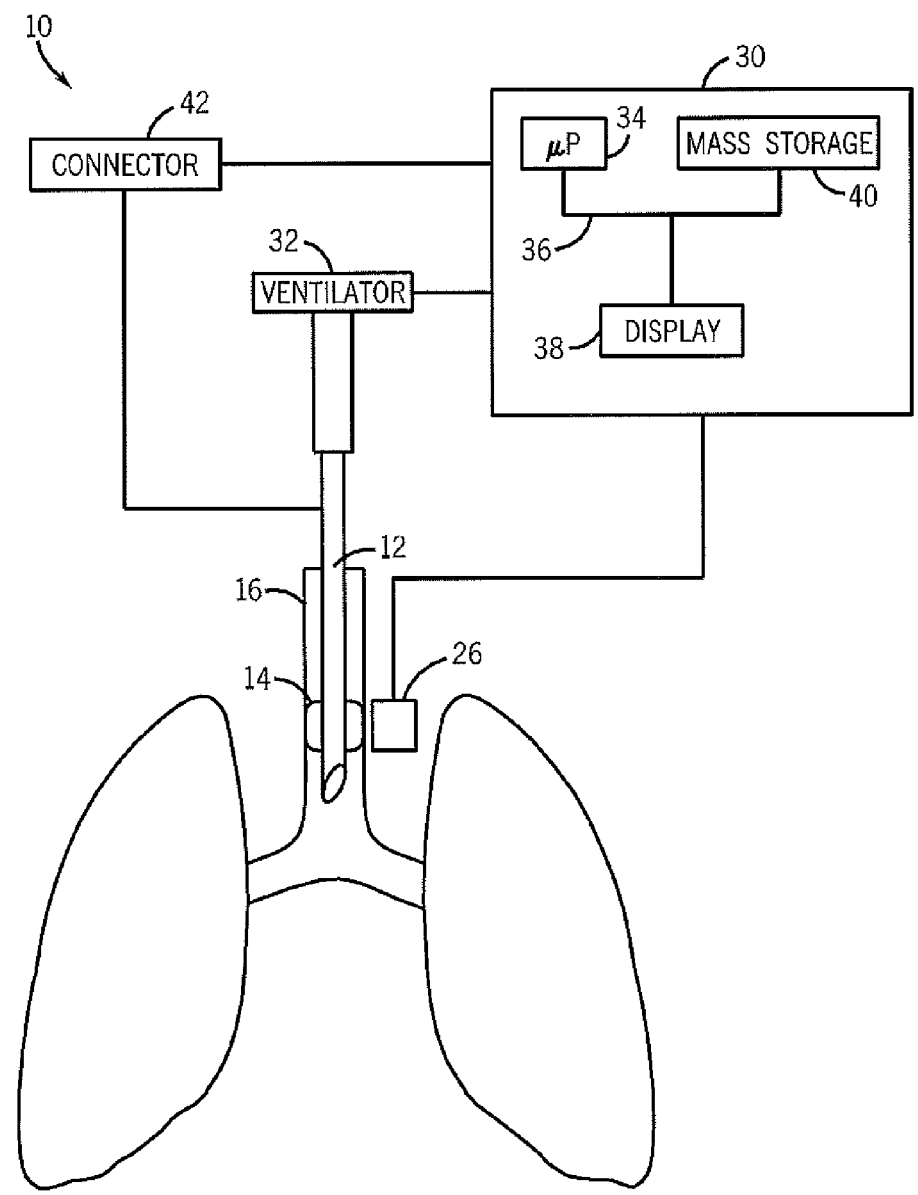
FIG. 1 illustrates an exemplary system including an endotracheal tube with a first pressure transducer and a second pressure transducer according to certain embodiments.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A tracheal tube may be used to seal a patient's airway and provide positive pressure to the lungs when properly inserted into a patient's trachea. Positioning the tracheal tube at a desired position within the trachea, for example during endotracheal intubation, may improve the performance of the tracheal tube and reduce clinical complications. In particular, the distal inserted end of the endotracheal tube may be positioned in the patient's trachea at a location substantially between the patient's vocal cords and carina. If the tube cuff is not inserted far enough past the vocal cords, for example, the tube may become more easily dislodged. If the tube is inserted too far into the trachea, such as past the carina, then the tube may only function to adequately ventilate one of the lungs, rather than both. Thus, proper placement of the distal tip of the tube generally results in improved ventilation to the patient.

Described herein are tracheal tubes and systems for facilitating proper placement of the tracheal tube relative to certain anatomical structures in and around the patient's airway and trachea. A healthcare provider may then use the information about the location of the tracheal tube relative to the anatomical structures (e.g., a patient's sternal notch) to determine whether the tube is properly placed or whether the position of the tube should be adjusted.

While ultrasound detection may be used to detect placement of endotracheal tubes within the trachea, the impedance mismatch between the tissue of the tracheal walls and the airspace in the trachea results in reflection of most of the signal back to the transducer and, thus, a low signal to noise ratio. In addition, the signal is weakened by the presence of muscle tissue and bone that prevent penetration of the signal into the trachea. Provided herein are tracheal tubes with balloon cuffs that include features to enhance ultrasound detection of the cuffs, for example by ultrasound transducers held against the patient's skin. The features allow the cuffs to be distinguished from the surrounding airspace of the trachea and the tracheal walls. Because balloon cuffs are inflated to touch the tracheal walls, ultrasound detection of the cuffs themselves, rather than the tube, prevents loss of signal to the surrounding airspace in the trachea, i.e., the ultrasound signal may pass from the tracheal tissue directly to the cuffs rather than being lost to the air. Accordingly, balloon cuffs with impedance that more closely matches the tissue of the trachea may be more easily detected without the reflectance loss that accompanies relatively large impedance mismatches between materials. From the position of the cuff, clinicians may determine information about the position of the tube itself, such as the location of the distal end of the tube. In addition, if the balloon cuffs as provided are probed by positioning the ultrasound transducer at a location such as the patient's sternal notch, which provides a signal path into the trachea relatively free of interfering anatomical structures, the resultant signal to noise ratio may be improved.

The disclosed tracheal tubes, systems, and methods may be used in conjunction with any appropriate medical device, including without limitation a feeding tube, an endotracheal tube, a tracheotomy tube, a circuit, an airway accessory, a connector, an adapter, a filter, a humidifier, a nebulizer, nasal cannula, or a supraglottic mask/tube. The present techniques may also be used to monitor any patient benefiting from mechanical ventilation, e.g., positive pressure ventilation. Further, the devices and techniques provided herein may be used to monitor a human patient, such as a trauma victim, an intubated patient, a patient with a tracheotomy, an anesthetized patient, a cardiac arrest victim, a patient suffering from airway obstruction, or a patient suffering from respiratory failure.

FIG. 1 shows an exemplary tracheal tube system 10 that has been inserted into the trachea of a patient. The system 10 includes a tracheal tube 12, shown here as an endotracheal tube, with an inflatable balloon cuff 14 including ultrasound detection features as provided that may be inflated to form a seal against the tracheal walls 16. In addition, the system 10 may include an ultrasound transmitter/receiver (e.g., a transducer) 26 to transmit signals into the trachea and receive the returned signals, which may be then communicated to a monitor 30 for further analysis.

The system 10 may also include devices that facilitate positive pressure ventilation of a patient, such as the ventilator 32, which may include any ventilator, such as those available from Nellcor Puritan Bennett LLC. As noted, the system 10 may also include monitor 30, which may be configured to implement embodiments of the present disclosure to determine information about the location of the tube 12 based upon the ultrasound signals transmitted into and then received from the cuff 14. In addition, the monitor 30 may be configured to calculate certain placement parameters of the tube 12 based on the position of the cuff relative to the placement of the ultrasound transducer 26. It should be understood that the monitor 30 may be a stand-alone device or may, in certain embodiments, be integrated into a single device with, for example, the ventilator 32.

The monitor 30 may include processing circuitry, such as a microprocessor 34 coupled to an internal bus 36 and a display 38. In one embodiment, the monitor 30 may be configured to communicate with the receiver 26, either through a cable connection or wirelessly. The transducer 26 may also provide calibration information to the monitor 30. Calibration information may be stored on a barcode or a separate memory circuit, such as a memory circuit or connector 42 associated with the tube 12. The information may then be stored in mass storage device 40, such as RAM, PROM, optical storage devices, flash memory devices, hardware storage devices, magnetic storage devices, or any suitable computer-readable storage medium. The information may be accessed and operated upon according to stored instructions for the microprocessor 34. The monitor 30 may be configured to provide indications of the placement parameters, such as an audio, visual or other indication.

Figure 2:
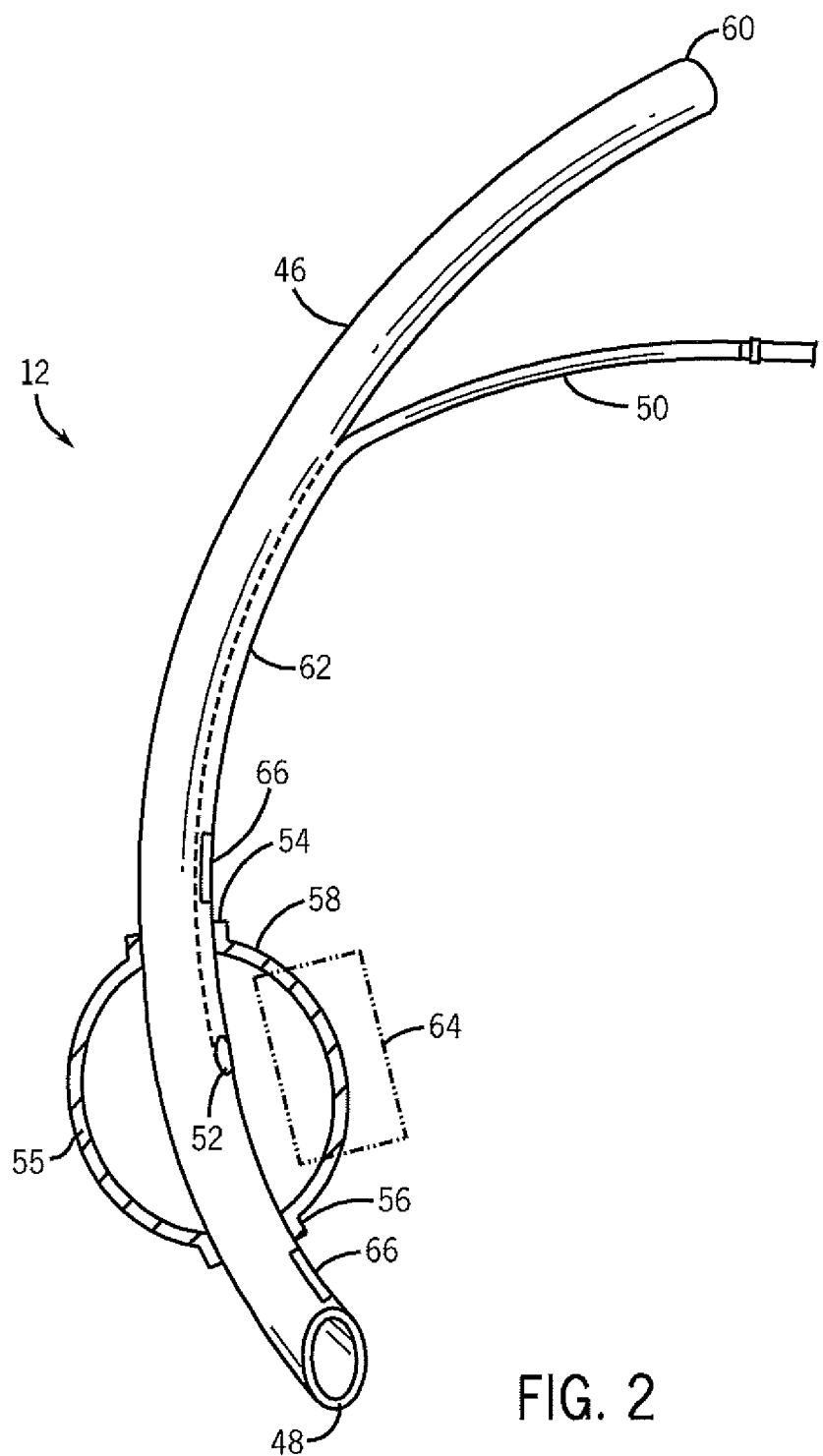
FIG. 2 is a perspective partial cutaway view of an endotracheal tube that may be used in conjunction with the system of FIG. 1 according to certain embodiments.

FIG. 2 is a perspective partial cutaway view of an example of a cuffed endotracheal tube 12 that may be used in conjunction with the system 10. The balloon cuff 14 is disposed on a conduit 46 that is suitably sized and shaped to be inserted into a patient and allow the passage of air through the airway path of the endotracheal tube 12. Typically, the cuff is disposed, adhesively or otherwise, towards the distal end 48 of the endotracheal tube 12. The balloon cuff 14 may, for example, be inflated and deflated via a lumen 50 in communication with the balloon cuff 14, typically through a hole or notch 52 in the endotracheal tube 12. The balloon cuff 14 includes a proximal collar region 54 and a distal collar region 56 formed in the cuff walls 55 and sized to accommodate the conduit 46 and used to mount the cuff 14 to the conduit 46. The collar regions 54 and 56 flank an inflatable region 58, which is in fluid communication with lumen 50.

Figure 3:
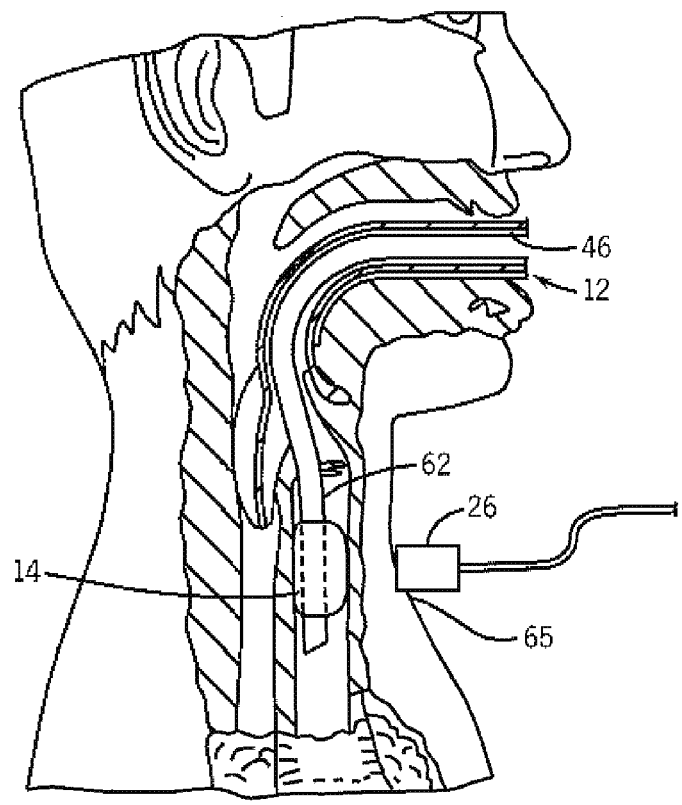
FIG. 3 is a side view of a tracheal tube inserted into a patient according to certain embodiments.

The endotracheal tube 12 may be configured to be inserted directionally into a patient's trachea. Not only is tube 12 configured to be inserted distal end 48 first, but the tube 12 may include a curve from the proximal end 60 to the distal end 48 that is designed to follow the contours of a typical patient's airway. Although this curve may be partially straightened out during insertion, the tube 12 will retain at least some of the curvature once inserted. Proper insertion of the tube 12 will typically result in the inside face of the curve 62 facing the patient's ventral, i.e., front, side. As shown in FIG. 3, curve 62 faces the sternal notch 65, which may be a location against which the ultrasound transducer 26 may be placed, the ultrasound-detectable features on the cuff 14 may be adapted to be aligned to correspond with the inside curve 62, e.g., to be located in region 64 of the cuff 14. When the cuff 14 is inflated, region 64 corresponds with the area of cuff that is closest to the patient's sternal notch 65.

Turning back to FIG. 2, in certain embodiments, the ultrasound-detectable features may be distributed all along or within the walls 55 of the cuff 14. However, in other embodiments, the ultrasound-detectable features may be distributed only within region 64 and not in other regions of the cuff 14. To ensure that these features are located as closely as possible to the measurement site outside the body when the tube 12 is in place, the tube 12 may include alignment features to allow any asymmetrically-distributed features of cuff 14 for ultrasound detection to be positioned correctly relative to the conduit 46. To ensure that region 64 is aligned with the inside curve 62 of the tube 12, the inside curve 62 may include one or more alignment indicators 66, which may be indicators of any type, including text, image, ink, chemical, or raised or shaped topographic markers, disposed on the inside curve 62 of the tube 12. The alignment indicators may be used to align the ultrasound-detectable features to the inside curve 62. In other embodiments, where the ultrasound transducer 26 is placed, for example, dorsally on the body, the alignment indicators 66 may be located on the tube 12 to align the ultrasound-detectable features to a location that will allow the features to contact the trachea on its dorsal side. Further, the cuff 14 may include additional alignment indicators. For example such alignment indicators may be useful in embodiments in which the ultrasound-detectable features are not visible to the naked eye or are otherwise difficult to align.

Figure 4:
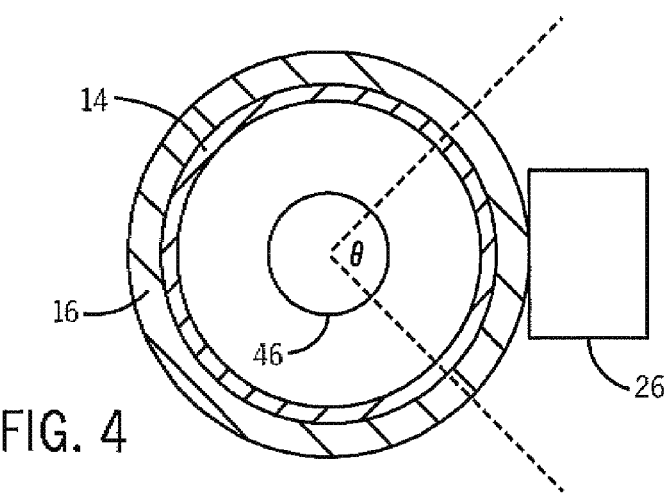
FIG. 4 is a top view of a tracheal tube inserted into a patient according to certain embodiments.

As noted, the ultrasound-detectable features may be distributed asymmetrically on the cuff 14. For example, they may be distributed on only a section of the cuff 14. FIG. 4 is a top down view of cuff 14 inflated against the tracheal walls 16. As noted, the ultrasound-detectable features may be distributed within and/or limited to a particular region, such as region 64, on the cuff 14. In other embodiments, the ultrasound-detectable features may be disposed along a circumferential section of the cuff 14 as viewed through a cross-section of the tube 12. The distribution of the ultrasound-detectable features may be, in embodiments, equal to or less than a 180° section, a 90° section, or a 60° section.

Figure 5:
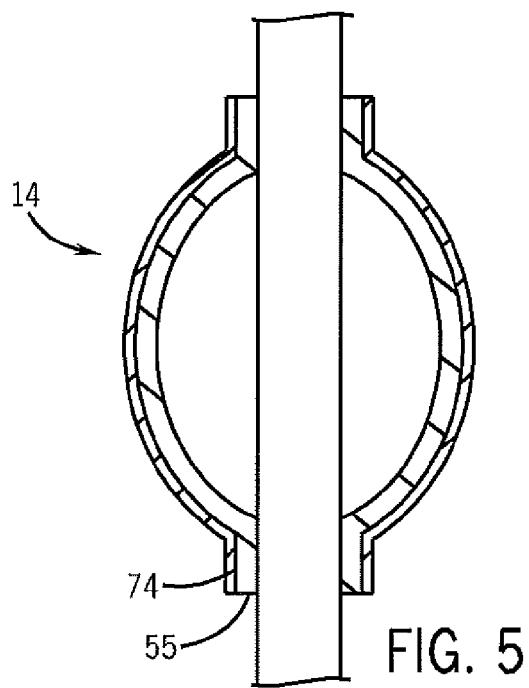
FIG. 5 is a side view of a tracheal tube cuff including an anti-reflective surface coating according to certain embodiments.

In particular embodiments, the ultrasound-detectable features in the cuff 14 may be incorporated within the cuff walls 55 or may be provided as a coating 74 on the cuff walls 55, either on the exterior patient side, as shown in FIG. 5, and/or as an interior coating (i.e., inside the inflatable region 58 of the cuff). For example, appropriate ultrasound-detectable features may include metals or other materials that more closely match the impedance of the cuff. In certain embodiments, the materials may be anti-reflective materials that are configured to reduce reflection of an ultrasound signal. Anti-reflective materials may include interference coatings (such as MgF2), silica coatings, titanium nitride, niobium nitride, or nanostructured coatings. Nanostructured coatings may include repeating nano bumps or protrusions that are smaller than the wavelength of light or sound used. In one embodiment, the anti-reflective materials may be configured to match the impedance of the balloon walls, e.g., the anti-reflective materials may have a refractive index within 20% of a square root of a refractive index of the balloon wall.

Figure 6:
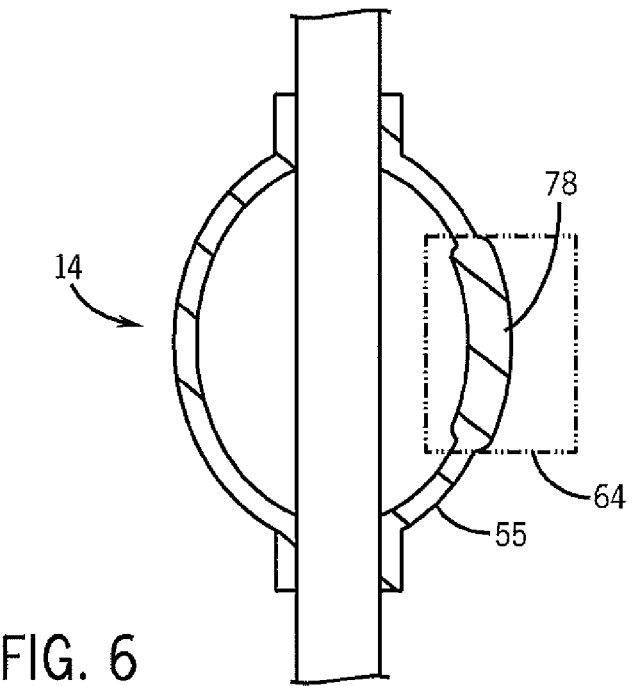
FIG. 6 is a side view of a tracheal tube cuff including a thick area in the balloon walls in a section of the cuff according to certain embodiments.
Figure 7:
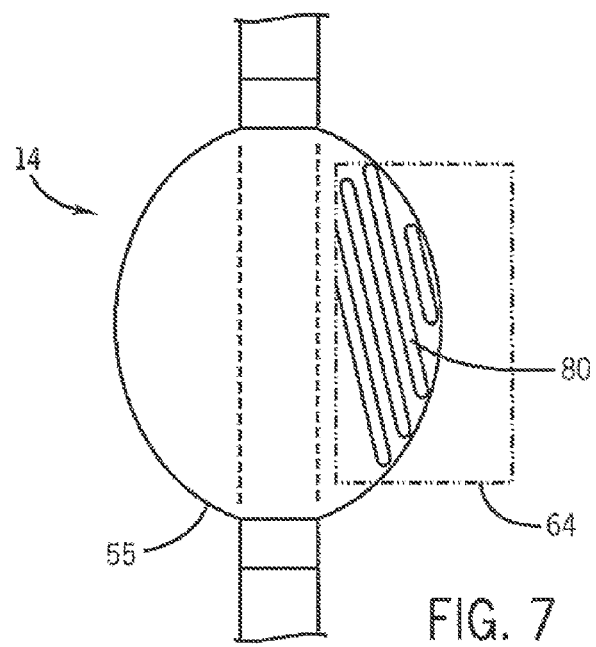
FIG. 7 is a side view of a tracheal tube cuff including a ridged or striped shaped area formed in the balloon walls according to certain embodiments.

In other embodiments, the ultrasound-detectable features may be formed of balloon wall material and may be thicker regions of the balloon wall 55. As shown in FIG. 6, a balloon wall may form a thick area 78 within region 64. For example, the balloon walls may be several millimeters in thickness within all or part of region 64, while the balloon walls 55 in the inflatable region 58 (but outside of region 64) may range in thickness from 0.015 mm±0.007 mm to about 1 mm in thickness. In an alternative embodiment, the ultrasound-detectable features may be shaped or patterned. FIG. 7 shows a cuff 14 with multiple ridges or stripes 80 formed from the balloon walls 55. As shown, the stripes 80 may be located at least in part within a particular portion of the cuff 14, such as within region 64.

Figure 8:
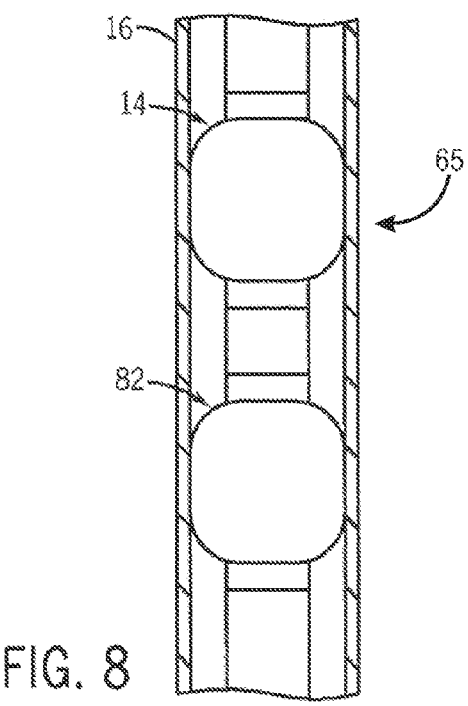
FIG. 8 is a side view of a tracheal tube inserted into a patient including a primary cuff and a secondary sealing cuff according to certain embodiments.

Often, clinicians may insert the tube 12 so that the cuff 14 is positioned at the sternal notch. However, depending on a patient's particular anatomy, the clinician may prefer to insert a sealing cuff just below the sternal notch. Because the sternal notch provides certain advantages for the placement of the ultrasound transducer 26, in such embodiments, the cuff 14 may be arranged to line up with the sternal notch while a second sealing cuff 82, as shown in FIG. 8, may be arranged on the tube 12 to be positioned correctly below the sternal notch. The cuff 14 may be primarily used for ultrasound detection and determination of the tube placement while the sealing cuff 82 may be used to seal the tracheal space. The cuff 14 may be only intermittently inflated, for example during initial placement determination or during any spot checking of tube placement.

The medical cuff 14 may be formed from materials having suitable mechanical properties (such as puncture resistance, pin hole resistance, tensile strength), chemical properties (such as forming a suitable bond to the conduit 46), and biocompatibility. In one embodiment, the walls of the inflatable cuff 14 are made of a polyurethane having suitable mechanical and chemical properties. An example of a suitable polyurethane is Dow Pellethane® 2363-90A. In another embodiment, the walls of the inflatable cuff 14 are made of a suitable polyvinyl chloride (PVC). Other suitable materials include polypropylene, polyethylene teraphthalate (PETP), low-density polyethylene (LDPE), silicone, neoprene, polyisoprene, or polyurethane (PU).

The cuffs 14 may be manufactured by any suitable process, such as by blow molding. In one example, a tube, such as an extruded polyurethane tube, is loaded into a blowing machine or mold assembly, such as a cross-section of a mold assembly that includes shapes in the mold corresponding to the desired shape of the detection features, e.g., thicker walls, ridges, or other shaped features. In addition, the mold may include alignment indicators, e.g., protrusions, depressions to line the detection features with a particular curve of the tube 12. In one embodiment, the mold assembly is manufactured from beryllium copper and includes a horizontal split in the assembly to allow opening and closing of the mold assembly. In an embodiment, the mold assembly may include mating symmetrical pieces that close together. The mold assembly may include integrated guide pins to prevent misalignment of the two mold halves. In one embodiment, the end-portions of an extruded tube that project out from the mold are constrained to the shape and thickness of the original extruded tube by non-heat transferable plastic holders at the ends of the mold. In one embodiment, the blow molders are model 2219H-LP blow molding machines, available from Interface Associates, that are configured to run at 1-2 bars of gas pressure.

Once loaded, the mold assembly is closed, and the tube is clamped at each end. The mold may then be heated. The tube may be stretched and air is blown into the tube via an air conduit, such as an air hose or nozzle, connected to a source of pressurized air, such as an air pump or pre-pressurized source, to achieve a desired positive pressure within the tube and to blow out the cuff walls to the shape of the mold assembly. Additional heat may be applied to the tube, such as via heating elements integral to the mold assembly to set the shape of the cuff 14. As the heat is applied, the stretch of the tube is relaxed and the air pressure within the tube is increased. Once the desired temperature is reached it is maintained for an interval of time. Afterward, the temperature of the mold assembly is allowed to drop or is actively cooled. A vacuum is applied within the tube, which now includes the blown cuff, to release the tube and cuff from the mold assembly and the tube and cuff are removed from the mold assembly.

For example, in one embodiment, a commercially available extrusion of Dow Pellethane® 2363-90AE having an inner diameter of 0.239±0.005 inches (6.0706±0.127 mm) and a wall thickness of 0.015 mm±0.007 mm may be blown to form a cuff 14 suitable for use with a 7.5 mm internal diameter (ID) endotracheal tube. The wall thickness may vary according to any specification for the detection features, e.g., the cuff walls 55 may be thicker or include certain shaped features. The extruded tube may be cooled to room temperature and, when set, inserted into the mold assembly automatically or by hand. Once loaded, the mold may be fitted into a sleeve of a blow-molding machine. The sleeve may be heated, such as by a series of ten electrical cartridges surrounding the sleeve, thereby heating the mold. In this embodiment, the mold may be heated to approximately 50° C. prior to stretching or blowing the extruded tube.

An air chuck locks on to one end of the extruded tube while the other end of the extruded tube is sealed by a clamp to create an airtight seal. The extruded tube is stretched by pulling on both ends of the tube and, while stretching, nitrogen or another suitable gas or gas mixture is into the extruded tube via the air chuck to pressurize the tube to between about 1 to about 3 bars. In one embodiment, the balloon will form in the portion of the tube situated within the mold when the tube expands under pressure to make contact with the internal walls of the mold.

When the cuff is fully blown against the inner walls of the mold, the mold may be heated (such as by heating the surrounding sleeve) to between about 100° C. to about 150° C. and this temperature may be maintained for between about 10 to about 30 seconds. After the application of heat, the mold may be cooled to approximately 45° C., such as by pumping refrigerated water at approximately 13° C. around the mold, to set the cuff. A vacuum is applied to the molded extrusion and cuff, and the extrusion and cuff are removed from the mold assembly. In embodiments in which an antireflective coating is disposed on the cuff, such coating may be applied to the finished cuff by any suitable method, including dipping, spraying, coextrusion during the extrusion process, sputter coating, etc. In other embodiments, the antireflective material may be mixed directly into the cuff material before the extrusion process.

While the disclosed embodiments may be susceptible to various modifications and alternative forms, specific embodiments have been shown by way of example in the drawings and have been described in detail herein. However, it should be understood that the disclosure is not intended to be limited to the particular forms disclosed. Rather, the disclosure is to cover all modifications, equivalents, and alternatives falling within the spirit and scope of the disclosed embodiments as defined by the following appended claims.

What is claimed is:

1. A system comprising:
   a tracheal tube comprising a conduit and configured to be inserted into a patient's airway;
   a balloon cuff associated with the conduit and comprising a balloon wall having a first portion configured to contact a ventral side of a tracheal wall and a second portion configured to contact a dorsal side of the tracheal wall, wherein the first portion has a first balloon wall thickness and the second portion has a second balloon wall thickness different from the first balloon wall thickness, wherein the first balloon wall thickness is greater than the second balloon wall thickness, wherein the first balloon wall thickness is only within a region of the first portion of the balloon wall that aligns with an inside curve of the tracheal tube, and wherein the region does not extend into the second portion of the balloon wall; an ultrasound transducer located outside the patient's body and configured to detect the first balloon wall thickness; and
   a monitor communicatively coupled to the ultrasound transducer and comprising a processor and a non-transitory mass storage device having stored instructions executable by the processor, wherein the instructions, when executed, are configured to determine a placement parameter of the conduit based on a position of the balloon cuff relative to a position of the ultrasound transducer.

2. The system of claim 1, wherein the balloon cuff is configured to contact the tracheal wall adjacent to a patient's sternal notch.

3. The system of claim 1, wherein the balloon cuff comprises polyethylene teraphthalate (PETP), low-density polyethylene (LDPE), polyvinyl chloride (PVC), silicone, neoprene, polyisoprene, polypropylene, or polyurethane (PU).

4. The system of claim 1, wherein the tracheal tube is operatively connected to a ventilator.

5. The system of claim 1, wherein the first portion comprises one or more protrusions and wherein the second portion is smooth.

6. The system of claim 1, comprising a second balloon cuff adapted to seal a patient's trachea.

7. The system of claim 1, wherein determining the placement parameter comprises receiving an ultrasound signal from the first balloon wall thickness on the balloon cuff, and wherein the ultrasound transducer transmits and receives the ultrasound signal.

8. A system comprising:
   a tracheal tube comprising a conduit;
   a balloon cuff associated with the conduit and comprising a balloon wall having a first portion configured to contact a ventral side of a tracheal wall and a second portion configured to contact a dorsal side of the tracheal wall, wherein the first portion comprises a pattern formed in a region of the first portion of the balloon wall not present on the second portion such that the pattern is only within the region of the first portion of the balloon wall, wherein the pattern is oriented non-orthogonally to an imaginary axis between a proximal and distal end of the balloon cuff, and wherein the region is aligned with an inside curve of the tracheal tube; and
   a monitor communicatively coupled to an ultrasound transducer located outside of a patient's body and configured to detect the pattern, the monitor comprising a processor and non-transitory mass storage device having stored instructions executable by the processor, wherein the instructions, when executed, are configured to determine a placement parameter of the conduit based on a position of the balloon cuff relative to a position of the ultrasound transducer.

9. The system of claim 8, wherein the pattern comprises ridges or stripes.

* * * * *